United States Patent
Chang

[11] Patent Number: 5,941,815
[45] Date of Patent: Aug. 24, 1999

[54] SIGMOID SPLINT DEVICE FOR ENDOSCOPY

[75] Inventor: Stanley F. Chang, Fresno, Calif.

[73] Assignee: Helix Medical, Inc., Carpinteria, Calif.

[21] Appl. No.: 09/113,414

[22] Filed: Jul. 10, 1998

Related U.S. Application Data

[63] Continuation of application No. 08/760,704, Dec. 5, 1996, Pat. No. 5,779,624
[60] Provisional application No. 60/045,201, Apr. 30, 1997, provisional application No. 60/055,545, Aug. 13, 1997, and provisional application No. 60/063,531, Oct. 29, 1997.

[51] Int. Cl.$^6$ .................................................. A61B 1/00
[52] U.S. Cl. ..................... 600/114; 600/201; 600/235; 604/167
[58] Field of Search ................................... 600/114, 129, 600/138, 139, 144, 153, 156, 184, 201, 208, 210, 235; 604/27, 48, 54, 73, 93, 160, 167, 239, 264, 278, 285, 256, 321, 336

[56] References Cited

U.S. PATENT DOCUMENTS

| | | | |
|---|---|---|---|
| 3,805,770 | 4/1974 | Okada | ........................................... 128/4 |
| 5,217,001 | 6/1993 | Nakao et al. | ................................ 128/4 |
| 5,259,366 | 11/1993 | Reydel | . |
| 5,337,733 | 8/1994 | Bauerfeind et al. | ......................... 128/4 |

OTHER PUBLICATIONS

Peter Cotton & Christopher Williams, "Practical Gastrointestinal Endoscopy," 4th ed., Blackwell Science Ltd (Oxford, England), p. 246–47, (Jul. 7, 1997).
Peter Cotton & Christopher Williams, "Practical Gastrointestinal Endoscopy," 2nd ed., Blackwell Scientific Publications (Oxford, England), p. 127–28.

*Primary Examiner*—Beverly M. Flanagan

[57] ABSTRACT

A splint or overtube device for use in keeping the sigmoid colon in a straightened position during endoscopy to facilitate advancement of the colonoscope or other types of medical endoscopes to the cecum. The present device utilizes an elongated member having a tight distal end or seal to close off the annular space between the endoscope and the elongated member at the distal end of the splint to prevent perforation of the colon. A hydrophilic lubricating substance can be utilized to minimize friction between the tight distal end or seal and the splint. An injection port is provided to allow the endoscope operator to inject fluid to lubricate the distal end or seal, to deflect away the colonic wall in advance of the splint and to remotely lubricate the scope distally. A second sealing member can be utilized at the proximal end of the splint to prevent loss of fluids from the splint.

36 Claims, 9 Drawing Sheets

SIGMOID SPLINT DEVICE FOR ENDOSCOPY

CROSS-REFERENCE TO RELATED APPLICATIONS

This application is a continuing application of U.S. patent application Ser. No. 08/760,704, filed Dec. 5, 1996, now U.S. Pat. No. 5,779,624, and claims the benefit of U.S. Provisional Application No. 60/045,201 filed Apr. 30, 1997, Ser. No. 60/055,545, filed Aug. 13, 1997, and Ser. No. 60/063,531, filed Oct. 29, 1997.

BACKGROUND OF THE INVENTION

1. Field of the Invention

The field of the present invention relates generally to devices for use in endoscopic examinations of the human colon. More specifically, the device described herein relates to medical equipment to facilitate the insertion of an endoscope into the human colon by keeping the sigmoid colon in a straightened position. Even more specifically, this device relates to splints or overtubes used over and in conjunction with an endoscope to maintain straightness of the sigmoid colon for the purpose of facilitating the insertion and movement of the endoscope through the sigmoid colon.

2. Background

As used herein, the term "splint" is used interchangeably with the term "overtube" to generally describe the device that is the subject of this patent. The term "endoscope" or "scope" is used to refer to a colonoscope, gastroscope, enteroscope, or other types of medical endoscopes. In referring to the opposite ends of the splint or scope, the "proximal end" means that part of the splint or scope which is closest to the operator or physician/surgeon performing the endoscopy and the "distal end" means that part of the splint or scope farthest from the operator or physician/surgeon.

Colonoscopy is the most sensitive and specific means for examining the colon, particularly for the diagnosis of colon cancers and polyps. Because the cecum, the portion of the colon furthest from the anus, is a common location for cancer, it is important that the entire colon be completely examined. In addition, Western countries have experienced a "rightward shift" of cancers of the colon in recent years as cancers of the right colon have become more common. However, because the anatomy of the colon can extremely vary from person to person, the technique of total colonoscopy is technically demanding.

During a colonoscopy, the scope is inserted in the anus, through the rectum, sigmoid colon, descending colon, transverse colon, ascending colon and then into the cecum. Advancing the scope, which is typically about 160 centimeters in length, can be difficult due to a loop in the sigmoid colon. Once the scope reaches the descending colon or transverse colon, this loop must be reduced by withdrawing the scope to a straightened position. Failure to straighten the loop in the sigmoid colon prior to continuing can cause enlargement of the loop and result in pain and damage, including adverse cardiac reactions such as hypotension and bradycardia. Once the loop is straightened, further advancement of the endoscope can usually be accomplished.

In patients having long sigmoid colons, reaching the cecum may be extremely difficult, if not impossible, due to reformation of the sigmoid loop when the operator attempts further advancement of the scope. Continued pushing of the scope under these circumstances enlarges the loop, rather than advancing the tip of the scope. Scope operators often employ various maneuvers to complete the examination, including changing the patient's position and the use of abdominal compressions. Unfortunately, these maneuvers prolong the procedure and are not always successful in helping the scope reach the cecum. Even expert colonoscopists experience difficulties in 10–20% of cases because of the long sigmoid colon problem. The overall success rate for total colonoscopy, i.e. getting the tip of the colonoscope to the cecum, has been reported to be 55–98%.

3. Related Art

The existing sigmoid splint has been in existence for over twenty years. When used correctly, it has proven to be a very helpful tool by allowing successful examination to the cecum, speeding up the procedure and making it less painful to the patient. The prior art splint is a hollow cylinder about 40 centimeters in length. It is made of a flexible but slightly rigid material, such as plastic, polyethylene, polyurethane, vinyl, or polyvinyl, of about 1 millimeter in thickness. The distal end of the prior art splint is tapered to an inner diameter about 4 millimeter greater than the scope. The proximal end has an outer diameter that is much larger than the distal end to prevent complete entry of the splint into the patient's body. The proximal end also has a rubber diaphragm with a hole slightly larger in diameter than the outside diameter of the scope to allow easy insertion of the scope through the splint.

In use during a colonoscopy, the colonoscope is inserted into the colon until further progress becomes difficult, at which time the tip of the colonoscope is typically located in the upper descending colon or the transverse colon. Using the colonoscope itself, the sigmoid loop is initially straightened. The splint, which should be placed over the proximal shaft of the colonoscope prior to beginning the examination, is gently pushed into the colon over the scope with the aid of lubricants, such as "JOHNSON & JOHNSON K-Y JELLY" (a registered trademark of Johnson & Johnson). With full insertion of the splint, the proximal end of the splint remains outside the anus, while the distal end is in the descending colon. The placement of the splint allows and maintains an almost straight-line passage from the anus to the descending colon. The colonoscope is then advanced while the splint is held stationary. The splint keeps the sigmoid in a straightened position, prevents a loop from reforming and facilitates advancement of the scope to the cecum.

Despite its advantages, the prior art splint is very rarely utilized due to the risk of perforation of the colon by the splint. Perforations are caused by the entrapment of a piece of colonic wall between the distal end of the splint and the endoscope when the splint is moved inside the patient's colon. The entrapment can occur either when the splint is advanced over the scope or when the scope is withdrawn through the splint. Once entrapped, a piece of colonic wall can be sheared off by the relatively sharp edge of the distal end of the splint. If the entrapped piece of colonic lining includes all layers of the colonic wall, then the tear becomes a through and through perforation. Alternatively, when the splint is advanced, carrying with it a piece of entrapped mucosa, the colonic wall behind it can be torn, also resulting in a perforation.

In the prior art devices, the space between the scope and the splint, approximately 2 millimeter in radius, has to exist to allow smooth movement of the scope and the splint against each other. Without this space, i.e., by modifying the prior art splint to have a tight fit for the scope, three undesirable features would occur: 1) too much friction would occur between the scope and the splint, causing resistance to manipulations; 2) damage to the scope as the splint rubs against the surface of the scope; and 3) the lubricant would be erased off the scope. In the invention which is the subject of the present patent, the space between the scope and the distal end of the splint is eliminated and the problems of friction to the movement of the endoscope against the splint, and its potential damage to the scope and the erasure of the lubricant, are avoided.

A safe sigmoid splint has very important applications in colonoscopy, and can lead to radical changes in the manner in which colonoscopy is performed. Currently, colonoscopes have to be fairly large (e.g., over 13 mm in outer diameter) in order to be able to produce the rigidity necessary to hold the sigmoid straight. Even with these large diameter, rigid scopes, the problem of reformation of the sigmoid loop still arises on a not infrequent basis. Reformation of the sigmoid loop not only causes great difficulties in advancing the tip of the scope, but is also extremely painful to the patient, such that intravenous sedation is almost always necessary. With a splint device, a much smaller colonoscope can be used, which could be almost painless to the patient. The reduction in pain results from reduced stretching of the sigmoid loop upon advancement to the descending colon and due to the sigmoid loop only being formed once during the procedure.

U.S. Pat. No. 5,337,733 to Bauerfeind, et al. describes a tubular inserting device with variable rigidity. This long overtube is made of two thin walls with space between. The outer wall is made of semi-rigid, non-expandable material, while the inner wall is made of material which is radially deformable, allowing expansion and resolution of the intervening space. Fluid is injected into the proximal end of the overtube to expand the space. When the space is expanded, the two walls separate from each other creating a flexible overtube. Suctioning out the injected fluid removes the space, bringing the two walls into contact with each other. The external surface of the inner wall and the internal surface of the outer wall are lined with a cogwheel like arrangement that engage and lock against each other when the space between them is removed, thereby producing a rigid overtube. When the space is expanded by injecting fluid, the two walls separate and the overtube returns to its flexible state.

The Bauerfeind, et al. overtube is introduced over the endoscope. During the colonoscopy procedure, when flexibility of the overtube is desired, the space between the two walls is expanded. When rigidity of the overtube is desired, this space is eliminated. The invention described by Bauerfeind, et al. in U.S. Pat. No. 5,337,733 does not address the issue of entrapment of colonic wall material between the distal edge of the splint and the scope. Tight-fitting seals, as described in the present invention, would not function properly in the Bauerfeind, et al. device, as it would create too much friction between the inside wall of the overtube and the endoscope. The present invention is much shorter, consists of only one wall and aims to address the problems caused by the space between the distal edge of the splint and the colonoscope.

Another invention, U.S. Pat. No. 3,805,770 to Okada, describes a ring-like device to hold the anus open for insertion of an endoscope past the anal sphincter. As with the Bauerfeind, et al. overtube, the Okada device does not utilize a tight-fitting seal and a tight-fitting seal would be detrimental to the proper function of the Okada invention. A tight-fitting seal would wipe off the lubricants placed on the endoscope, thereby defeating the very purpose for utilizing the device disclosed by Okada.

Another invention, U.S. Pat. No. 5,259,366 to Reydel, describes an endoscopic treatment procedure that utilizes a catheter sleeve assembly that slides along the outer surface of an endoscope to provide at least one lumen for inserting medical instruments into the patient's body. This device does not utilize a sealing mechanism to prevent colonic wall entrapment and is not intended to straighten the sigmoid colon.

Yet another invention, U.S. Pat. No. 4,601,283 to Chikama, describes the use of a wire made of memory shape alloy. This wire is inserted into the biopsy channel of the scope. By keeping the wire at certain temperatures, it returns and remains in its "memorized" straight shape, keeping the endoscope in a straightened position. The present invention avoids the necessity of the special wire and avoids the resultant possible damage to the biopsy channel, which has been reported to occur.

SUMMARY OF THE INVENTION

The sigmoid splint or overtube in accordance with the present invention solves the problems associated with the related art devices described above. That is to say, the present invention provides a sigmoid splint or overtube that is effective in straightening the sigmoid during an endoscopic procedure to allow easy insertion of the scope while avoiding damage to the colon.

In the preferred embodiment, the sigmoid splint of the present invention is of tubular shape and made of a flexible but somewhat rigid material such as rubber, latex, plastic, polyethylene or polyurethane, or other similar materials, alone or in combination, with or without an embedded wire mesh material to enhance its rigidity. The stiffness of the splint can be non-uniform throughout its length, in that the stiffness can vary from its distal end to its proximal end. The shaft may be made of heat-sensitive material, with varying degrees of rigidity at different temperatures. It may also be made of heat-retaining material to maintain warmth for patient comfort. Typically, the length of the splint will be 20 to 80 centimeters, however the splint can be the entire length of the scope and/or be adjustable in length (i.e., telescoping or accordion-shaped). A balloon device can be fitted along the shaft to adjust its rigidity. The preferred length for the splint is about 40 centimeters. Its distal end has an inner diameter substantially equal to or up to several millimeters greater than the outside diameter of the scope. If the diameter is substantially equal to the outside diameter of the scope, then the distal end of the splint functions as the distal seal, as described herein. If the diameter is greater than the outside diameter of the scope, then a separate distal seal is required. The proximal end of the splint has an outside diameter larger than the outside diameter of the distal end in order to prevent complete entry of the splint into the patient's body. Although the preferred embodiment consists of a straight tube, the device can also be pre-shaped or made with a shape and/or rigidity that changes upon approaching body temperature.

In the preferred embodiment, the inner surface of the distal end of the splint has a seal made of a substantially pliable material. The material for the seal can be absorbent and/or elastic. Examples of such materials include sponge and foam rubber. Alternatively, the device can utilize the end of the tube itself, either straight or with a lip or other configuration, to prevent colonic wall entrapment. When used, the thickness of the distal seal should be substantially equal to or slightly greater than the gap between the scope and the splint, providing an opening substantially equal to or slightly smaller than the outer diameter of the endoscope; such that when the scope is passed through it, the fit will not allow entrapment of colonic mucosa. The seal can begin at and/or protrude beyond the distal end of the splint. In the preferred embodiment, the portion extending beyond the splint has a tapered, streamlined configuration, producing a tapered end for the splint to facilitate its insertion into the colon. The more proximal portion of the seal is attached to the inner surface of the distal portion of the splint or in continuity with the distal end of the splint. The length of this seal can be from 1 millimeter, or less, to the entire length of the splint. That is, the distal seal itself may have the configuration of a hollow cylinder-like structure. To ease insertion of the scope, which has a blunt end, into the splint, the proximal end of the seal can also be tapered.

The distal end, whether it is a tight fit or a separate seal, should be well lubricated. Although other lubricants may also be suitable, a preferred lubricant is a hydrophilic substance, similar to that used to line glide-type guide wires, for example, the "TERUMO" (a registered trademark of Terumo Corporation) guide wire. These hydrophilic substances have the unique property of becoming extremely slippery when wet with water or saline. An adequate layer of the hydrophilic substance should be coated and/or impregnated into the distal end and/or seal, typically by the manufacturer. Water or an aqueous solution that is applied to the end or seal will cause the sliding surface to become extremely slippery, allowing easy passage of the scope past the distal end. The use of a well lubricated distal end or seal in the present invention closes the potentially hazardous gap between the distal end of the splint and the scope while preventing undue friction, thereby allowing safe, easy and damage-free movement of the scope.

An injection port can be located at or near the proximal end of the splint for fitting a syringe. This port allows the injection of water or lubricant into the splint during an endoscopy, in order to periodically add wetness and lubrication to the surface of the distal end and/or seal, the splint and the scope itself. As set forth below, the injection port also allows the injection of fluid, including air, to expand or deflect the colon ahead of the splint to further ease insertion of the splint. Without the injection port, or an equivalent mechanism to deliver fluid to inside the splint, lubrication of the distal end and/or seal is dependant upon the lubricating fluid remaining on the scope, which may be an unreliable source.

Small longitudinal grooves can be made on the inner surface of the distal end or seal to allow fluid that has been injected or infused into the splint through the injection port to exit from the distal end of the splint. These grooves can cut through the entire thickness of the seal, structuring the seal in a non-continuous fashion. The injection of fluid deflects away the colonic wall ahead of where the splint is being inserted, thus further assuring that the colonic wall will not become entrapped by the distal end of the splint. Injected water or an aqueous solution can also exit via these grooves, so that any potentially adherent colonic wall can be kept off the distal end of the splint. An aqueous based lubricant can be injected through the port to lubricate the distal end or seal and that portion of the endoscope that is beyond the distal end, thereby easing insertion of the endoscope through the colon beyond the sigmoid area.

The proximal end can also be fitted with a seal. The proximal seal should be made of a substantially pliable material. Examples of such materials include sponge and foam rubber. It can be a similar or different material from that used for the distal seal. The thickness of the proximal seal can be substantially equal to or slightly greater than the gap between the scope and the splint, creating an opening substantially equal to or slightly smaller than the outer diameter of the endoscope, such that when the scope is passed through it, a tight fit is produced. A tight-fitting proximal seal will guide the scope through the splint and prevent loss of fluids that are injected through the injection port into the endoscope/splint annulus. As with the distal seal, the proximal seal should be coated or impregnated with a lubricant, such as a hydrophilic substance to avoid problems with excessive friction.

To further ease insertion of the scope through the splint, the inside surface of the splint itself can be likewise coated or impregnated with a lubricant. As with the distal and proximal seals, a hydrophilic substance would be a good lubricant, as long as the coated surface can be kept in a wetted condition during the endoscopic procedure.

A bullet-tip device can be fitted over the end of the scope at the time of inserting the scope through the splint, before the scope is introduced into the patient to further facilitate insertion of the scope through the splint. Once the scope tip comes out of the seal, this bullet device is removed, and the scope/splint combination is ready for insertion into the patient's body. In cases where the scope needs to be removed and then reintroduced into the patient, such as removal of multiple polyps from the proximal colon, the splint may remain in the colon while the scope is removed. In these instances, the scope can be reintroduced into the splint by inserting a balloon catheter into the scope. The balloon is inflated once it exits the scope. By configuring the balloon in a roughly conical shape, the scope is similarly introduced through the splint inside the patient's colon. Once the tip of the scope exits the distal end of the splint, the balloon is deflated and removed from the scope.

Aside from applications in colonoscopy, the splint or overtube of the present invention can be applicable to other medical or non-medical procedures. The device of the present invention may also have useful applications in the upper gastrointestinal tract or other parts of the human anatomy.

Accordingly, the primary objective of the present invention is to provide a safe, effective and relatively easy to use device for facilitating the insertion and use of an endoscope during an endoscopy procedure.

It is also an important objective of the present invention to provide a sigmoid splint or overtube suitable for straightening and maintaining the straightness of the sigmoid colon during endoscopy.

Another important objective of the present invention is to provide a sigmoid splint or overtube having a lubricated tight distal end or seal at its distal end to seal the annular area around the endoscope to prevent entrapment of colonic mucosa.

Yet another important objective of the present invention is to provide a sigmoid splint or overtube having an injection port suitable for injecting fluids to lubricate the tight distal end or seal and the endoscope so as to ease insertion past the sigmoid colon or to inject air or fluid to expand or deflect the area of the colon ahead of the device.

Another important objective of the present invention is to provide a sigmoid splint or overtube having a seal at its distal end to seal the annular area around the endoscope and ease entry into the colon and a second seal at its proximal end to prevent loss of fluids out of the splint and to guide the endoscope through the splint.

BRIEF DESCRIPTION OF THE DRAWINGS

In the drawings which illustrate the best modes presently contemplated for carrying out the present invention:

FIG. 5A through 5D shows use of the splint during a colonoscopy procedure;

DETAILED DESCRIPTION OF THE PREFERRED EMBODIMENTS

With reference to the figures where like elements have been given like numerical designations to facilitate understanding the present invention, and particularly with reference to the embodiments of the present invention illustrated in FIGS. 1 through 6, the sigmoid splint device is designated generally 10. The sigmoid splint 10 includes an elongated tubular member 12 with an outer surface 14 and an inner surface 16. Tubular member 12 has a distal end 18 which enters the human body and a proximal end 20 which has a mechanism for preventing complete entry into the human body during the procedures described herein, such as an outside diameter at the proximal end 20 being larger than the outside diameter of distal end 18. The inside diameter of tubular member 12 must be greater than the outside diameter of the endoscope to be used with splint 10.

Tubular member 12 can be shapes other than tubular, for instance member 12 can be oval or any other shape that permits easy entry into and passage through the colon. The stiffness of splint 10 can vary along its length. For example, the distal end 18 can be more flexible than the remaining portion of the splint to facilitate easy insertion of splint 10 into the human colon. Outer surface 14 of tubular member 12 can include a plurality of insertion markings (not shown) at spaced apart intervals to indicate the depth of insertion of tubular member 12 into the colon.

Located at or near the distal end 18 of tubular member 12 is distal seal 22 having an opening 23, an external surface 24 and an internal surface 26. In the preferred embodiment, the external surface 24 of distal seal 22 attaches to inner surface 16 of tubular member 12. Also in the preferred embodiment, the diameter of opening 23 should be substantially equal to or slightly less than the outer diameter of the endoscope, such that distal seal 22 closes on the endoscope to prevent entrapment of colonic wall material between the endoscope and splint 10. The tightness of distal seal 22 should be such that the interface of the seal and the endoscope will not entrap mucosa and/or will not allow the free flow of fluid from inside the splint. For lubrication purposes, it may be beneficial if the interface of the seal and the endoscope will allow some fluid to trickle out onto the portion of the endoscope beyond the splint. Distal seal 22 should be made of a pliable material.

Figure 1:
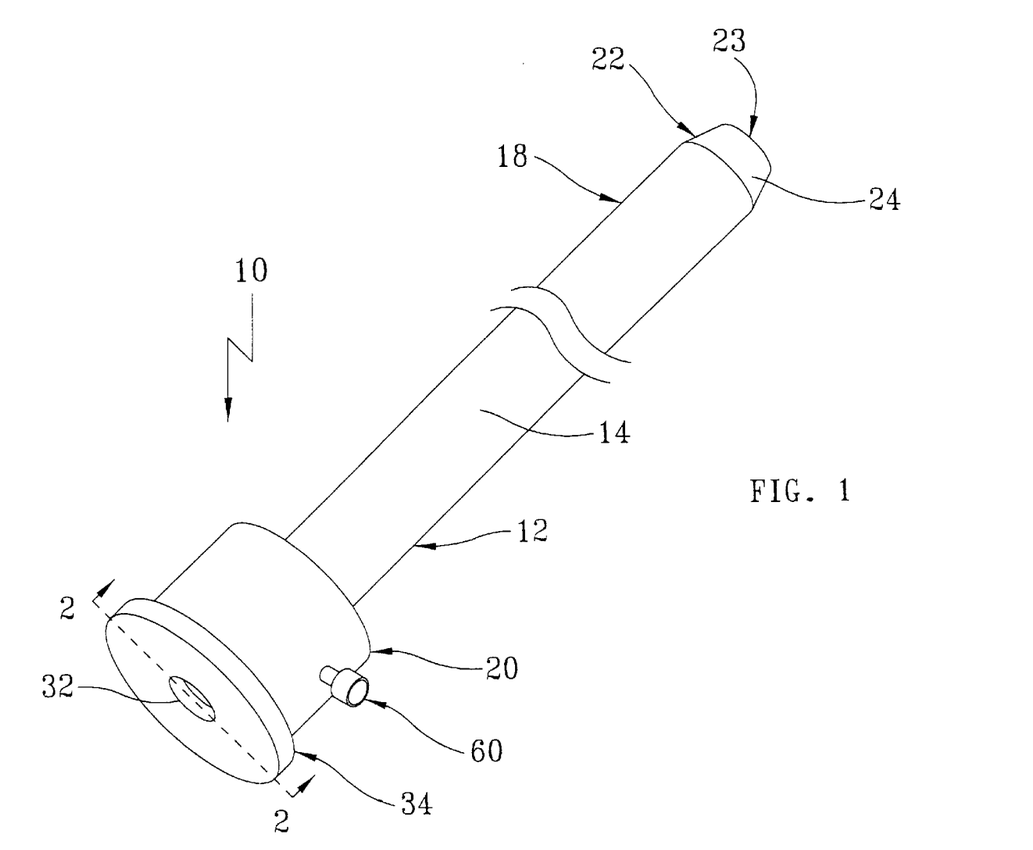
FIG. 1 is a perspective view of the sigmoid splint device that is the subject of this patent.
Figure 2:
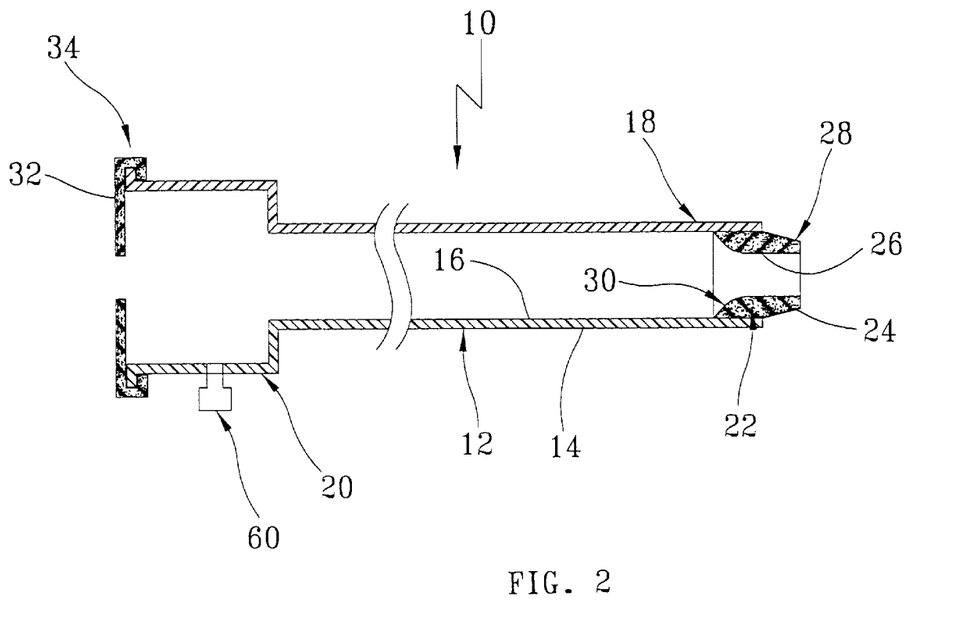
FIG. 2 is a cross-sectional view of the device in FIG. 1, showing the proximal end cap and an elongated and tapered distal seal.

In the preferred embodiment, as shown in FIGS. 1 and 2, distal seal 22 is elongated and extends beyond distal end 18 of tubular member 12. As also shown in FIGS. 1 and 2, the preferred embodiment utilizes distal seal 22 having both ends tapered. The forward taper 28 extending beyond the distal end 18 facilitates insertion of the splint 10 into the colon and further prevents undesirable capture of the colonic wall between the splint and the endoscope. The rearward taper 30 facilitates passage of the endoscope through the splint 10.

Figure 3:
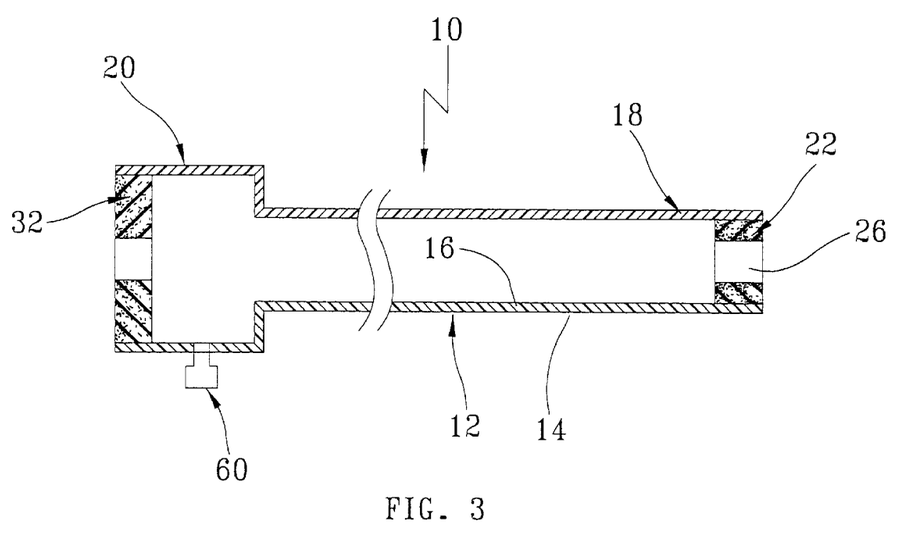
FIG. 3 is a cross-sectional view of the embodiment with ring-like sealing structures at both the distal and proximal ends of the splint.

As shown in FIG. 3, distal seal 22 can be ring-like in configuration, i.e., not tapered, and located entirely inside distal end 18 of tubular member 12. Even in this configuration, when the endoscope is inside sigmoid splint 10, distal seal 22 seals the annular space around the endoscope to prevent loss of fluid from inside tubular member 12 and to prevent the colonic wall from being trapped between the endoscope and splint 10. In an alternative embodiment, distal end 18, having distal seal 22, is detachable from tubular member 12. The connection between a detachable distal end 18 and tubular member 12 must be smooth to protect the patient.

Alternatively, distal seal 22 can be integral with the distal end 18 of tubular member 12. The seal 22 can be made of the same material as tubular member 12 and can merely be a continuation of distal end 18 (this would be similar to the distal end in FIGS. 1–3 without the separate distal seal shown). Alternatively, distal seal 22 can be an inwardly formed lip (not shown) at distal end 18 of tubular member 12. If distal seal 22 is an integral part of tubular member 12, an injection mechanism (described below) must be utilized to ensure seal 22 remains sufficiently lubricated to prevent excessive friction against the outer surface of the endoscope. The hydrophillic substance discussed above is a good lubricant for a tight distal end. Fluid from the injection mechanism can keep the distal end sufficiently wet to keep it in a slippery condition. Alternatively, if the endoscope and splint can be disposed in fluid while in the colon (i.e., an aqueous based fluid placed in the colon prior to or during the endoscopic procedure), the injection mechanism would not be required. Distal seal 22 can, whether integral with or separate from tubular member 12, be made of material that creates a tight seal only upon exposure to body temperature or injected fluids (i.e., the material for seal 22 expands to narrow opening 23).

Figure 4A:
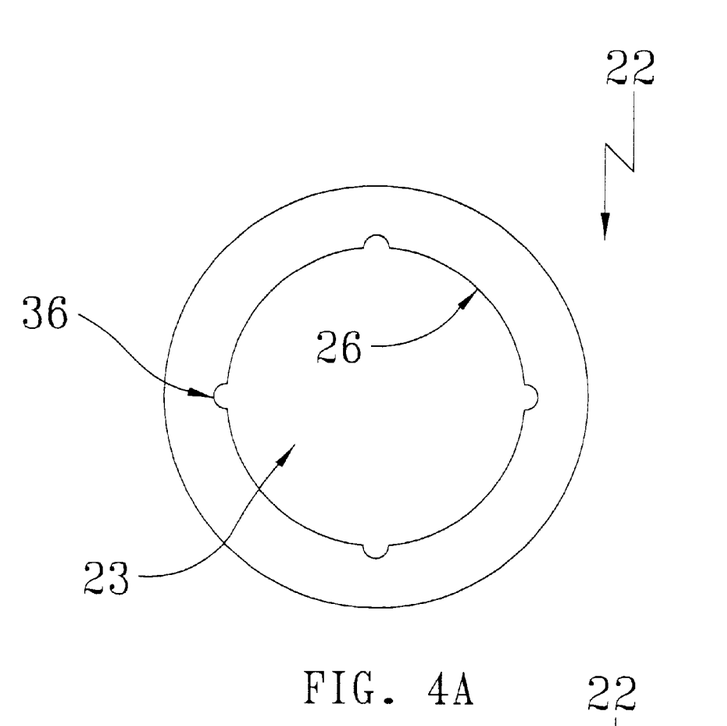
FIG. 4A is a cross-sectional view of the distal seal with longitudinal grooves cut into the distal seal.
Figure 4B:
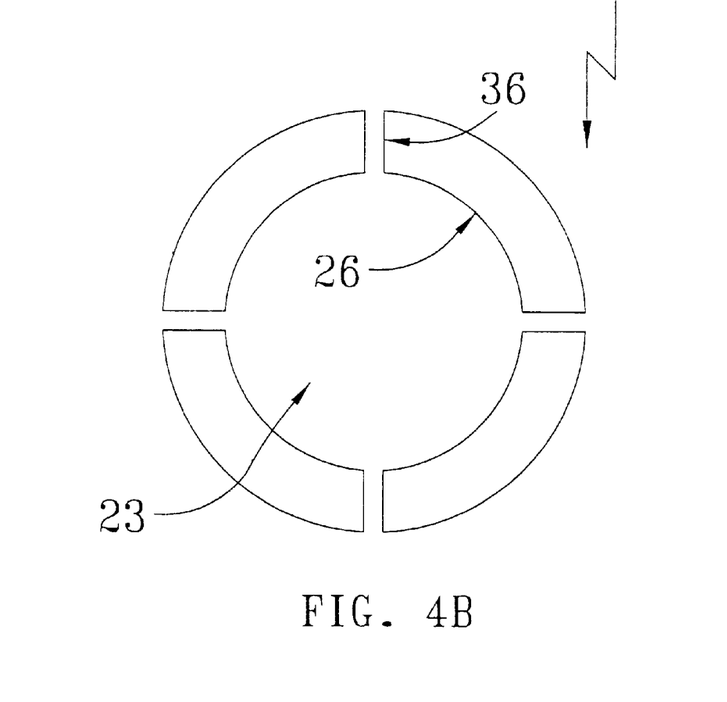
FIG. 4B is a cross-sectional view of the distal seal with longitudinal grooves cut entirely through the distal seal.

FIGS. 4A and 4B show the use of longitudinal grooves 36 in distal seal 22 to allow the passage of fluid around distal seal 22 when the endoscope is inside splint 10. FIG. 4A shows small longitudinal grooves 36 only partially cut into distal seal 22. FIG. 4B shows longitudinal grooves 36 cut entirely through distal seal 22. In either configuration, longitudinal grooves 36 would extend over the entire length of distal seal 22. The ability to pass fluids through or around distal seal 22 allows the introduction of wetting fluids into tubular member 12 to ensure distal seal 22 is sufficiently moist to facilitate smooth movement of the endoscope. Longitudinal grooves 36 also permit the introduction of fluid into and through tubular member 12 to expand or deflect the colon ahead of the endoscope, clear unwanted colonic wall from distal end 18 of tubular member 12 and deliver aqueous based lubricants to the portion of the scope beyond distal end 18 of tubular member 12. Alternatively, distal seal 22 can incorporate one or more openings within the body of the seal 22 to allow fluid to pass through distal seal 22 and accomplish the objectives set forth above. Longitudinal grooves 36 can also be used when a tight distal end embodiment is used to accomplish results similar to those discussed above.

The grooves in the distal seal can have a straight, branched or angulated pattern. Because of the force of gravity, when the grooves are longitudinal and straight, the injected fluid may not exit the distal seal in an even fashion along the circumference of the seal. A modified design can be implemented to allow the injected fluid to be distributed evenly as it exits the distal seal.

An injection port 60 can be located at or near proximal end 20 of the tubular member 12 to allow the introduction of fluids, such as water or lubricants into the splint 10 to wet distal seal 22 to ensure it remains in a pliable and slippery condition and to provide additional lubrication to scope 38 while inside splint 10 and beyond distal end 18 of splint 10. The additional lubrication of scope 38 while in the colon beyond splint 10 will further ease passage of scope 38 through the colon. Injection port 60 also allows the injection of fluid through tubular member 12 and into colon 40 to expand or deflect colon 40, further easing insertion of splint 10, and to clear a path through colon 40 for tubular member 12. Injection port 60 can be in fluid communication with the annular space between splint 10 and endoscope 38 when endoscope 38 is engaged in splint 10 and be suitable for attachment to a syringe or other device that allows controlled injection of fluids. Alternatively, injection port 60 can connect to a separate tube, channel in tubular body 12, or other similar devices (not shown) that can be provided along inner surface 16 or inside the body of tubular member 12 to deliver the aqueous-based solution to distal seal 22 and beyond. Any such device must be sufficiently small so as to not interfere with the movement of endoscope 38 inside splint 10.

Figure 5A:
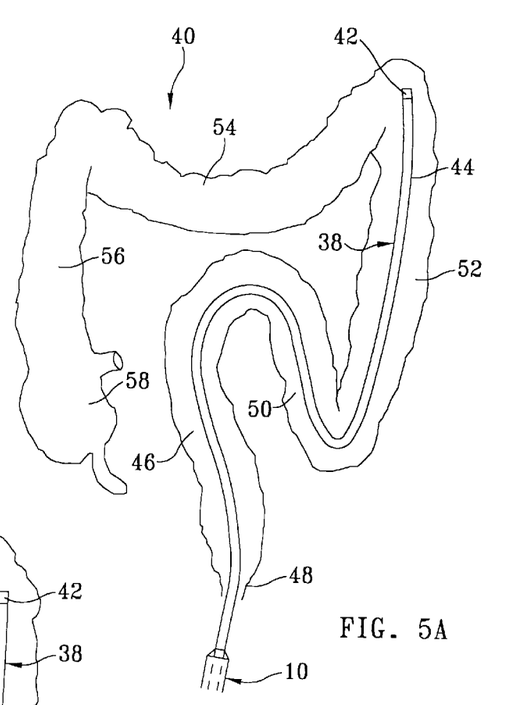
Figure 5B:
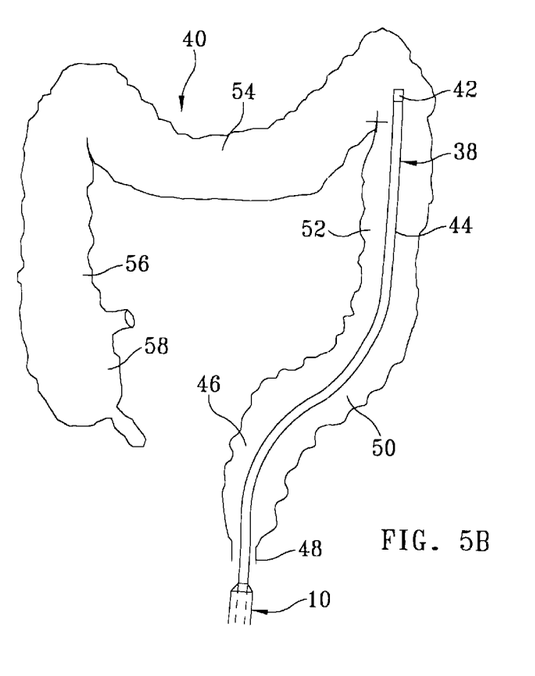
Figures 5C, 5D:
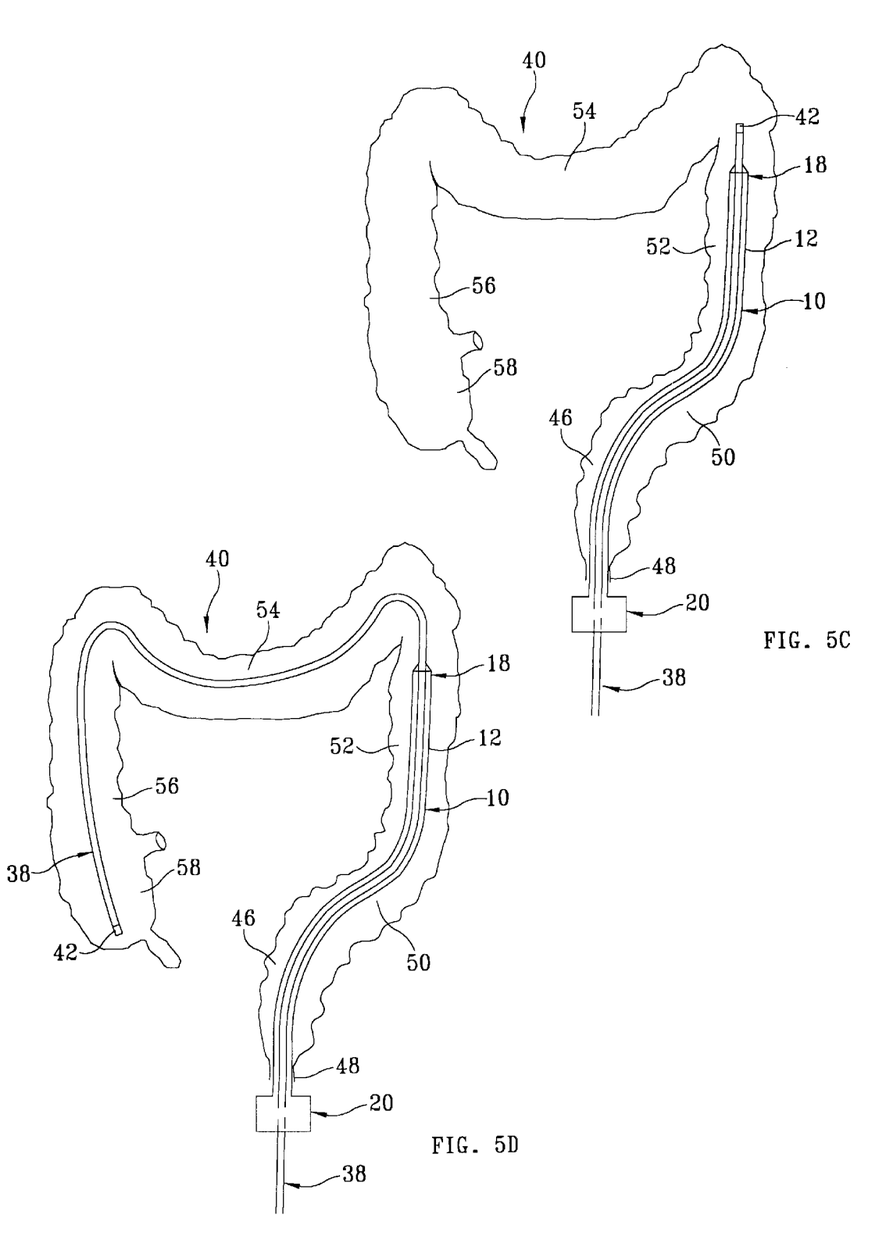

In use during a colonoscopy, as shown in FIGS. 5A through 5D, the colonoscope 38 is initially inserted or pre-loaded into the splint 10 prior to beginning the procedure to investigate the colon 40. After lubricating endoscope 38 with a first lubricant, tip 42 and body 44 of endoscope 38 is introduced into the rectum 46 through the anus 48 and then into the sigmoid colon 50. After negotiating the loop in the sigmoid colon 50, the endoscope 38 enters the descending colon 52. Further advancement of tip 42 is made easier by partially withdrawing endoscope 38 to straighten the sigmoid colon 50 with body 44 of endoscope 38 (as shown in FIG. 5B). Once the sigmoid colon 50 is straightened, distal seal 22 and the outer surface of distal end 18 of tubular member 12 are lubricated with a second lubricant (which could be the same as the first lubricant). After lubrication, tubular member 12 is slid over endoscope 38, through the anus 48 and into the rectum 46, the sigmoid colon 50 and then the descending colon 52 (as shown in FIG. 5C). Proximal end 20 of tubular member 12 remains outside the anus 48. The presence of splint 10 inside the sigmoid colon 50 and descending colon 52 prevents reformation of the loop, thereby facilitating further insertion of the endoscope 38 through the transverse colon 54 and ascending colon 56 and then into the cecum 58 (as shown in FIG. 5D). During the further insertion of endoscope 38, splint 10 is held in place. After completing the desired medical procedure, endoscope 38 is withdrawn to the transverse colon 54 while holding splint 10 in place. Splint 10 is withdrawn from the patient and then endoscope 38 is withdrawn from the patient.

When injection port 60 is utilized, a supply of fluid, such as an aqueous-based solution, is connected to injection port 60 prior to insertion of splint 10 into anus 48. After splint 10 is in place, the aqueous-based solution is injected into the annulus between splint 10 and endoscope 38 and out distal end 18 of splint 10 to deflect away the colonic wall ahead of splint 10. While inserting endoscope 38 into the remaining portion of the colon, the aqueous-based solution is slowly injected into the annulus to continue to provide additional lubrication to the portion of endoscope 38 beyond splint 10. During the withdrawal of endoscope 38, the aqueous-based solution can be slowly injected into the annulus to provide lubrication and keep the colonic wall away from distal end 18 of tubular member 12. If a hydrophillic substance is used to coat or impregnate distal seal 22, the lubricant must be wetted prior to use and must be kept in a wetted condition during the entire procedure.

If no injection port 60 is used yet the distal end or seal 22 is coated or impregnated with a lubricant such as a hydrophillic substance, which must be kept in a wetted condition to function as a lubricant, the colon 40 should be filled or partially filled with fluid prior to the procedure. The patient is placed on his or her left side so that the descending colon 52 is at the bottom. The descending colon 52 is filled or partially filled with an aqueous solution or other suitable wetting solution after wetting the coated distal end or seal 22. In this manner, the fluid in the colon 40 will provide the wetting solution to keep the lubricant in a wetted condition. Sufficient fluid must remain in the colon 40 during the entire procedure.

An alternative embodiment of the present invention includes the use of a mechanism to prevent fluid from discharging out the proximal end 20 of tubular member 12, particularly when injection port 60 is utilized with the tight distal seal 22. One such mechanism is the use of a second seal, proximal seal 32, at or near proximal end 20 of tubular member 12 to seal the space between the inner surface 16 and the outside diameter of the endoscope. Although proximal seal 32 is not mandatory for splint 10 to properly function, proximal seal 32 can prevent loss of fluid from inside splint 10. As shown in FIGS. 1 and 2, proximal seal 32 can be incorporated into an end cap 34 that attaches to the proximal end 20 of tubular member 12. End cap 34 and proximal seal 32 can be a single-piece rubber diaphragm that removably attaches to proximal end 20. As shown in FIG. 3, proximal seal 32 can also be ring-like and be located entirely within proximal end 20 of tubular member 12 to guide the endoscope and prevent loss of fluids out tubular member 12. Alternatively, splint 10 can utilize a hose or other flow passage device (not shown), including a passageway incorporated into the wall of splint 10, to deliver fluid directly from injection port 60 to distal end 18. Such a flow passage device can deliver fluid to lubricate distal seal 22 and the endoscope beyond the distal end 18 of splint 10, while preventing loss of fluid out proximal end 20 of tubular member 12.

Figure 6:
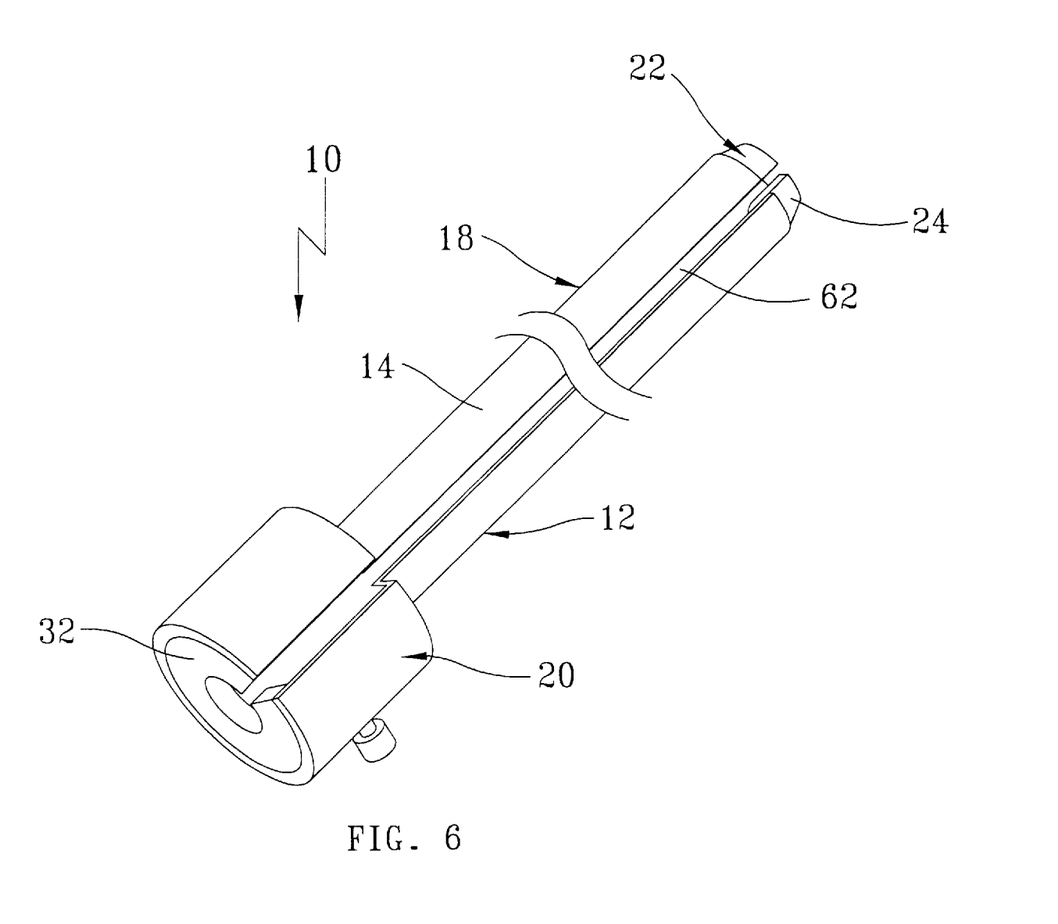
FIG. 6 shows a tubular member with a longitudinally oriented open-ended slot.

Another embodiment of the present invention, shown in FIG. 6, utilizes a longitudinally oriented open-ended slot 62 on tubular member 12. The slot is sized to removably receive endoscope 38. With this embodiment, the endoscope 38 does not have to be inserted or pre-loaded onto sigmoid splint 10 prior to inserting scope 38 into the patient, thereby allowing the full length of scope 38 to be utilized for manipulations. After the scope is introduced into the descending colon 52 or transverse colon 54, it is straightened in the usual fashion by reducing the sigmoid loop. Splint 10 is then loaded onto scope 38 by opening slot 62. After loading, slot 62 can be closed by sealing it with adhesive tape or by utilizing a locking mechanism either on or in tubular member 12, as described below. The other components of this embodiment, other than slot 62, are identical to the embodiments described above and it is used during an endoscopy examination as set forth above.

Aside from a straight slot 62, splint 10 can have a slot 62 of other configurations to accomplish the objectives set forth in the applications. These configurations include slanted, oblique, curved and saw-toothed. Yet other configurations are also possible.

Figure 7:
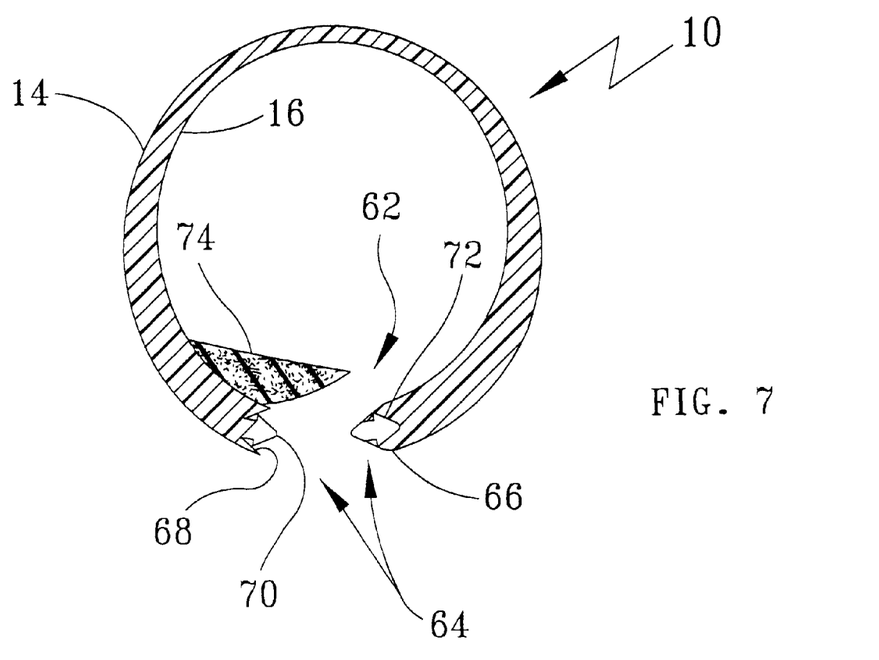
FIG. 7 is a cross-sectional view of an alternative embodiment of the splint showing the non-uniform thickness of the tubular member taken at the location of a locking mechanism.
Figure 8:
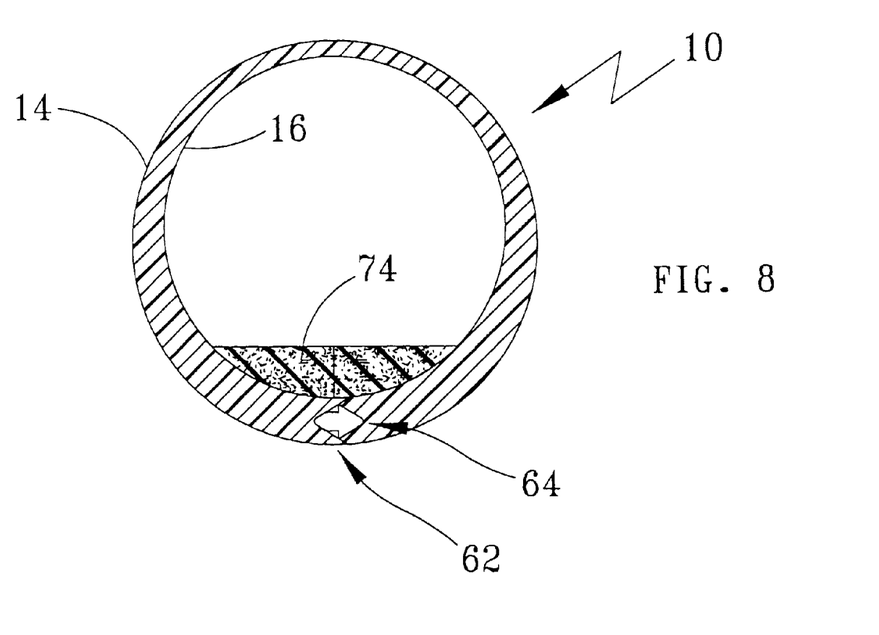
FIG. 8 is a cross-sectional view of the alternative embodiment of the splint shown in FIG. 7 with the slot shown in a closed position.

The typical splint, when closed, has a cross-section of a hollow cylinder having a thin circular wall of uniform width. The present invention can be modified such that the thickness of the wall of the hollow cylinder is non-uniform. For instance, on cross-section, one side of splint 10 can have a greater thickness than the rest of the circular ring, as shown in FIGS. 7 and 8. Although this will cause splint 10 to be more ovoid, rather than circular, in cross-section, it will not disturb its intended function. An ovoid shaped splint, particularly if the wall of splint 10 is thicker and thus stiffer on one side, can have the advantage of allowing the physician to twist the splint to stiffen it if he or she is having difficultly.

Longitudinal slot 62 can be incorporated into the thickened aspect of the circular wall. Having extra thickness allows the installation of locking sealing mechanism 64. One such sealing mechanism is shown in FIGS. 7 and 8, and described herein. In cross-section, the apposing edges of the slot can have a V-shaped, W-shaped or saw-tooth configuration, with one edge being convex, and the other edge concave. Convex edge 66 fits snugly into concave edge 68. The wall of the splint, along one or both of these edges, can be made of a flexible, slightly deformable, and elastic material such as rubber. When the two edges are brought tightly together, a water-tight seal is formed, much like the washer used with the typical garden hose.

Incorporated into the two edges, at suitable spacing intervals as viewed longitudinally along the length of slot 62, are one or more locking mechanisms 64 to seal slot 62 in a closed position. One example of such a locking mechanism, shown in FIGS. 7, is a series of spear or arrow-head shaped studs 70 which fit snugly into openings 72 at the opposing edge of slot 62. If studs 70 and openings 72 are appropriately sized and configured such that studs 70 lock into openings 72, slot 62 can be closed by a squeezing action that "snaps" studs 70 into openings 72. Slot 62 is thus held securely closed in all three dimensions.

To allow sufficient size for slot 62 when it is opened, so as to easily place endoscope 38 into splint 10, it is best if studs 70 do not project out into the opening of slot 62. It is therefore preferred, although not required, that studs 70 be incorporated into concave side 68 of the two edges, while openings 72, which house studs 70 upon closure of slot 62, are incorporated on convex side 66. A configuration having studs 70 and openings 72 on the opposite sides of slot 62 than that described above is also possible.

Concave side 68 should have smooth, rounded edges at the inner 16 and outer 14 surfaces of splint 10. That is, the two top ends of the V-shaped edge should be rounded off to avoid a cutting action by these edges against the colon on the outside, and against scope 38 on the inside. With the design of the splint/slot combination described herein, the safety and the water-tight features of the sigmoid splint 10 are preserved without having to use the sleeve described below.

One or more longitudinal strips of cushioning material 74, as shown in FIGS. 7 and 8, can be configured to be on opposite sides of slot 62, between the splint and the scope. Strips 74 are made of absorbent and deformable material, such as foam rubber. Strips 74 are installed onto inner surface 16 of splint 10. Each of strips 74 are attached to inner surface 16 of splint 10 along the edge of longitudinal slot 62. The side of each strip 74 closest to the edge of slot 62 should conform to the shape of slot 62. Strips 74 can be flush with slot 62, protrude slightly or be recessed slightly. Thus, when slot 62 is closed, strips 74 protect scope 38 from any cutting or rubbing damage when it is moved against the edges of slot 62 and minimize leakage of the injected fluid from the closed slot 62. Strips 74 can, alternatively, be a single piece of material that attaches at one end to inner surface 16 with the other end extending perpendicular through slot 62 such that when slot 62 is closed the strip 74 folds over and covers the slot joint, thereby further protecting the patient.

Strips 74 can have the length of splint 10, (i.e., such that their ends are attached to the proximal and distal seals). Strips 74 can be made of material that is the same as the proximal and/or distal seals. The width of strips 74 can be 1 mm or more. The thickness of strips 74 should be less than the gap between scope 38 and splint 10. To facilitate use of strips 74, the cross-section of splint 10 can be made into a slightly ovoid shape, as shown in FIGS. 7 and 8, in order to allow a roughly equal space between scope 38 and splint 10 circumferentially.

Figure 9:
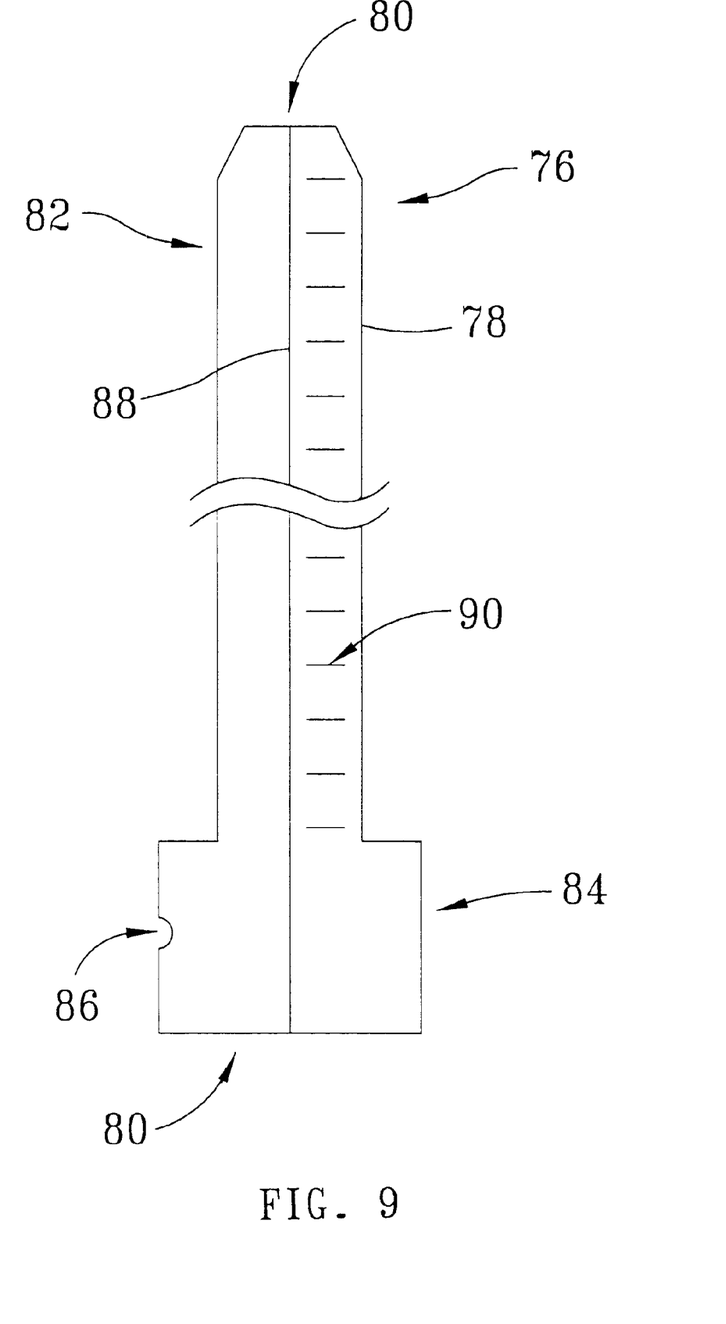
FIG. 9 shows a sleeve that can be utilized with the splint of the present invention.

In another alternative embodiment, shown in FIG. 9, sleeve 76 is provided to enclose and tightly house splint 10. Sleeve 76 is in the form of tubular member 78 with circular openings 80 at each end. Sleeve 76 is made of a thin, flexible material such as rubber, latex, plastic or other similar material or a combination thereof. Its function is to enclose and cover the outer surface 14 of splint 10 and, when used with the slotted embodiment, to hold slot 62 together once splint 10 is loaded onto scope 38.

Distal end 82 of sleeve 76 can be slightly tapered. Shaft 78 is of a uniform width, except its proximal aspect 84 consists of a short segment of a larger diameter. When pulled over splint 10, sleeve 76 covers splint 10 with a snug fit. At its proximal aspect 84, a slit or a roughly circular opening 86 is provided to expose injection port 60.

At the start of the colonoscopy procedure, sleeve 76 is first loaded onto scope 38 in the proper orientation, in an accordionated configuration, in order to not interfere with the manipulation of scope 38. Once scope 38 is in descending colon 52 or above, and when it is determined that splint 10 is needed, splint 10 is loaded onto scope 38 by opening and then closing its slot 62, in a position proximal to sleeve 76. Sleeve 76 is then pulled over splint 10, with the aid of a small quantity of lubricant if necessary. By utilizing sleeve 76, slot 62 will remain sealed to protect the patient from the edges of slot 62 and any fastening or locking devices 64 placed on or around it. Sleeve 76, when used with the slotted splint device offers the great advantage of not having to be pre-loaded, while maintaining the integrity, safety and dependability of the slotless splint.

In order to allow accurate placement of slit or opening 86 for injection port 60, a longitudinal marking 88 is printed along the length of sleeve 76. When sliding sleeve 76 over splint 10, the operator assures that line 88 is placed directly over closed slot 62, so that when sleeve 76 is completely pulled over splint 10, slit or opening 86 of sleeve 76 allows exposure of and access to injection port 62. At various intervals along the length of sleeve 76 can be placed a plurality of depth markings 90 to indicate the depth of sleeve 76, and therefore splint 10, inside the colon. The opening 86, when placed around injection port 60, also serves to anchor the sleeve 76 against splint 10.

While there is shown and described herein certain specific alternative forms of the invention, it will be readily apparent to those skilled in the art that the invention is not so limited, but is susceptible to various modifications and rearrangements in design and materials without departing from the spirit and scope of the invention. In particular, it should be noted that the present invention is subject to modification with regard to the dimensional relationships set forth herein and modifications in assembly, materials, size, shape, and use.

What is claimed is:

1. A splint device for use in medical endoscopy to guide an endoscope having an outer diameter, comprising:

an elongated member having an outer surface, an inner surface, a distal end and a proximal end, said distal end having a first outside diameter and said proximal end having a second outside diameter means for preventing complete entry of said elongated member into a human body during the medical endoscopy; and means for preventing complete entry of said elongated member into a human body during the medical endoscopy; and first sealing means at said distal end for sealing the annular space between said elongated member and the endoscope when the endoscope is inside said elongated member, said first sealing means having an opening, said opening having a diameter substantially equal to or slightly smaller than the outer diameter of the endoscope.

2. The splint device according to claim 1, wherein said elongated member is tubular.

3. The splint device according to claim 1, wherein said first sealing means is a seal attached to said inner surface of said elongated member.

4. The splint device according to claim 1 further comprising injection means located near said proximal end of said elongated member for injecting fluid into said tubular member.

5. The splint device according to claim 4 further comprising delivery means connected to said injection means for delivering fluid to and beyond said distal seal.

6. The splint device according to claim 4, wherein said first sealing means is integral with said elongated member.

7. The splint device according to claim 1, wherein at least one of said first sealing means and said inner surface of said elongated member is coated or impregnated with a lubricant.

8. The splint device according to claim 7, wherein said lubricant is a hydrophilic substance.

9. The splint device according to claim 1, wherein said first sealing means extends beyond said distal end of said elongated member.

10. The splint device according to claim 1, wherein said first sealing means further comprises passage means for allowing fluid to pass through said distal end of said elongated member when the endoscope is engaged in the splint.

11. The splint device according to claim 1 further comprising second sealing means located at said proximal end of said elongated member for sealing the annular space between said inner surface of said proximal end and the endoscope when the endoscope is inside said elongated member, said second sealing means having an opening.

12. The splint device according to claim 11, wherein said opening of said second sealing means has a diameter substantially equal to or slightly smaller than the outer diameter of the endoscope.

13. The splint device according to claim 11, wherein said second sealing means is integral with said elongated member.

14. The splint device according to claim 11, wherein at least one of said first sealing means, said inner surface of said elongated member and said second sealing means is coated or impregnated with a lubricant.

15. The splint device according to claim 14, wherein said lubricant is a hydrophilic substance.

16. The splint device according to claim 1 further comprising a longitudinally oriented slot in said elongated member for removably receiving the endoscope and closure means for closing said slot when the endoscope is in said elongated member.

17. The splint device according to claim 16 further comprising slot sealing means attached to said elongated member for sealing said slot.

18. The splint device according to claim 1 further comprising a sleeve member having a flexible tubular body with opposing open ends.

19. The splint device according to claim 1, wherein said first sealing means has one or more tapered ends.

20. The splint device according to claim 1, wherein said preventing means comprises said second outside diameter being greater than said first outside diameter.

21. A splint device for use in medical endoscopy to guide an endoscope having an outer diameter, comprising:

a semi-rigid elongated tubular member having an outer surface, an inner surface, a distal end and a proximal end, said distal end having a first outside diameter and said proximal end having a second outside diameter;

means for preventing complete entry of said elongated member into a human body during the medical endoscopy;

first sealing means located at said distal end for sealing the annular space between said elongated member and the endoscope when the endoscope is inside said tubular member, said first sealing means having an opening, said opening having a diameter slightly smaller than or substantially equal to the outer diameter of the endoscope; and injection means near said proximal end of said tubular member for injecting fluid into said tubular member.

22. The splint device according to claim 20 which further comprises second sealing means located at said proximal end for sealing the annular space between said inner surface of said proximal end and the endoscope when the endoscope is inside said tubular member.

23. The splint device according to claim 21, wherein at least one of said first sealing means and said inner surface of said elongated member is coated or impregnated with a lubricant.

24. The splint device according to claim 23, wherein said lubricant is a hydrophilic substance.

25. The splint device according to claim 21 further comprising a sleeve member having a flexible tubular body with opposing open ends and a port opening, said port opening sized and configured to provide access to said injection means.

26. The splint device according to claim 21, wherein said elongated member further comprises a longitudinally oriented slot for removably receiving the endoscope and closure means for closing said slot when the endoscope is in said elongated member.

27. The splint device according to claim 24 further comprising a sleeve member having a flexible tubular body with opposing open ends and a port opening, said flexible tubular body having a marking corresponding with the position of said slot when said splint is engaged in said sleeve, said port opening sized and configured to provide access to said injection means.

28. The splint device according to claim 21, wherein said preventing means comprises said second outside diameter being greater than said first outside diameter.

29. A method of using a sigmoid splint having a tight-fitting distal seal to help introduce an endoscope through the sigmoid colon into the proximal colon to perform a medical procedure, comprising the steps of:

(a) lubricating the endoscope with a first lubricant;

(b) introducing the endoscope into the rectum through the anus and then beyond the sigmoid colon having a sigmoid loop;

(c) partially withdrawing the endoscope so as to straighten the sigmoid colon with the endoscope;

(d) lubricating said distal seal and the outside surface of said splint with a second lubricant;

(e) inserting said splint over the endoscope through the anus into the rectum, sigmoid colon and descending colon to prevent reformation of the sigmoid loop;

(f) advancing the endoscope through the proximal colon while holding said splint in place;

(g) performing the desired medical procedure;

(h) withdrawing the endoscope to the transverse colon while holding said splint in place;

(i) withdrawing said splint; and (j) withdrawing the endoscope.

30. The method of using a sigmoid splint to introduce a medical instrument through the sigmoid colon recited in claim 29 further comprising the steps of connecting a supply of aqueous-based solution to the splint and injecting said aqueous-based solution into the annular space between the splint and the endoscope prior to insertion of the splint, injecting said aqueous solution into the splint while advancing the endoscope to the cecum, and injecting said aqueous solution into the splint while withdrawing the endoscope from the colon.

31. The method of using a sigmoid splint to introduce a medical instrument through the sigmoid colon recited in claim 29 further comprising the step of placing said splint over the endoscope prior to introducing the endoscope into the rectum.

32. The method of using a sigmoid splint to introduce a medical instrument through the sigmoid colon recited in claim 29 further comprising the steps of loading the endoscope in said splint through a slot in said splint after straightening the sigmoid colon with the endoscope and closing said slot after the endoscope is in the splint prior to inserting said splint into the anus.

33. The method of using a sigmoid splint to introduce a medical instrument through the sigmoid colon recited in claim 32 further comprising the step of sealing said slot with an adhesive tape after closing said slot.

34. The method of using a sigmoid splint to introduce a medical instrument through the sigmoid colon recited in claim 32 further comprising the steps of placing a sleeve over said splint and aligning an alignment mark on said sleeve with said slot prior to inserting said splint into the anus.

35. A method of using a sigmoid splint that has been coated or impregnated with a hydrophilic substance to introduce a medical instrument through the sigmoid loop in the colon to the cecum to perform a medical procedure, comprising the steps of:

wetting the coated or impregnated portions of said splint with an aqueous-based solution;

placing the instrument through said splint;

connecting a supply of aqueous-based solution to said splint;

introducing the medical instrument into the rectum through the anus and then into the sigmoid colon having a sigmoid loop;

inserting one end of the medical instrument into the descending colon;

partially withdrawing the medical instrument so as to straighten said sigmoid loop;

inserting said splint over the medical instrument through the anus into the rectum, sigmoid colon and descending colon while injecting said aqueous-based solution into the annular space between said splint and the medical instrument to wet the surfaces of said splint coated or impregnated with said hydrophilic substance and to lubricate the medical instrument;

advancing the medical instrument through the descending colon, transverse colon, ascending colon and into the cecum while performing the medical procedure;

withdrawing the medical instrument to the transverse colon after completing the medical procedure;

withdrawing said splint from the colon; and withdrawing the medical instrument.

36. A method of using a sigmoid splint that has been coated or impregnated with a hydrophilic substance to introduce a medical instrument through the sigmoid loop in the colon to the cecum to perform a medical procedure, comprising the steps of:

wetting the coated or impregnated portions of said splint with an aqueous-based solution;

placing the instrument through said splint;

placing aqueous-based solution in said colon;

introducing the medical instrument into the rectum through the anus and then into the sigmoid colon having a sigmoid loop;

inserting one end of the medical instrument into the descending colon;

partially withdrawing the medical instrument so as to straighten said sigmoid loop;

inserting said splint over the medical instrument through the anus into the rectum, sigmoid colon and descending colon while said splint is disposed in said aqueous-based solution in said colon to wet the surfaces of said splint coated or impregnated with said hydrophilic substance and to lubricate the medical instrument;

advancing the medical instrument through the descending colon, transverse colon, ascending colon and into the cecum while performing the medical procedure;

withdrawing the medical instrument to the transverse colon after completing the medical procedure;

withdrawing said splint from the colon; and withdrawing the medical instrument.

* * * * *